US008202417B2

(12) United States Patent
Vinkovic et al.

(10) Patent No.: US 8,202,417 B2
(45) Date of Patent: Jun. 19, 2012

(54) CHIRAL STATIONARY PHASES FOR CHROMATOGRAPHY BASED ON AROMATIC ALLYL AMINES

(75) Inventors: Vladimir Vinkovic, Zagreb (HR); Darko Kontrec, Zagreb (HR); Goran Landek, Zagreb (HR)

(73) Assignee: Rudjer Boskovic Institute (HR)

( * ) Notice: Subject to any disclaimer, the term of this patent is extended or adjusted under 35 U.S.C. 154(b) by 4 days.

(21) Appl. No.: 12/961,292

(22) Filed: Dec. 6, 2010

(65) Prior Publication Data
US 2011/0094966 A1    Apr. 28, 2011

Related U.S. Application Data

(63) Continuation of application No. PCT/HR2009/000006, filed on Feb. 26, 2009.

(30) Foreign Application Priority Data

Mar. 7, 2008    (HR) .............................. P 20080102 A

(51) Int. Cl.
    B01D 15/08    (2006.01)
(52) U.S. Cl. ..................... 210/198.2; 210/635; 210/656; 210/502.1; 502/401
(58) Field of Classification Search ........... 210/635.656, 210/659, 198.2, 502.1; 502/401, 402
See application file for complete search history.

(56) References Cited

U.S. PATENT DOCUMENTS

| 5,674,387 A | * | 10/1997 | Pirkle et al. | ................ | 210/198.2 |
| 2001/0050254 A1 | * | 12/2001 | Welch et al. | ................. | 210/635 |
| 2004/0144708 A1 | * | 7/2004 | Kontrec et al. | ............ | 210/198.2 |

FOREIGN PATENT DOCUMENTS

| WO | 9306080 A1 | 4/1993 |
| WO | 9606080 A1 | 2/1996 |
| WO | 9639377 A1 | 12/1996 |
| WO | 0000464 A1 | 1/2000 |
| WO | 02070124 A1 | 9/2002 |

OTHER PUBLICATIONS

Uray, et al.; "(S,S)-Diphenyl-ethanediamine (DPEDA) Derivatives as Chiral Selectors Part I. Undecenoyl Bound Dinitrobenzoyl-DPEDA as a Broadly Applicable Chiral Stationary Phase 1)"; Chromatographia, vol. 30, No. 5/6, 1990, pp. 323-327.

Hyun, et al.; "A Chiral Recognition Mechanism Proposed for Resolving Pi-Acidic Racemates on Pi-Acidic Chiral Stationary Phases Derived From (S)-Leucine"; J. High Resol. Chromalogr. vol. 21, 464-470 (1998).

(Continued)

*Primary Examiner* — Ernest G Therkorn
(74) *Attorney, Agent, or Firm* — St. Onge Steward Johnston & Reens LLC

(57) ABSTRACT

New chiral stationary phases (CSPs) based on chiral selectors covalently bound on a solid support were prepared. Chiral selectors were obtained from enantiomerically pure aromatic amines and 3,5-dinitrobenzoic acid and then linked to the support surface through the allylic double bond. Such obtained materials allow enantioseparation of racemates or enantiomerically enriched compounds. These chiral stationary phases can be used as fillings in chromatographic columns for enantiomer separation of naproxen type drugs and other similar non-steroidal anti-inflammatory drugs (NSAID) by means of high performance liquid chromatography on both the analytical and preparative scale.

7 Claims, 6 Drawing Sheets

OTHER PUBLICATIONS

C. Allenmark, "Chromatographic Methods and Enantioseparation Application", 2nd. ed., New York, Ellis Norwood, 1991.

Uray, et al.; "Comparison of Chirasil-DEX CB as Gas Chromatographic and ULMO as Liquid Chromatographic Chiral Stationary Phase for Enantioseparation of Aryl- and Heteroarylcarbinols"; Journal of Chromatography A, 992 (2003) 151-157.

Brewer, et al.; "Determination of Enantiomeric Composition by Negative-Ion Electrospray Ionization-Mass Spectrometry Using Deprotonated N-(3,5-Dinitrobenzoyl)amino Acids as Chiral Selectors"; Chirality 17:456-463 (2005).

Maier, et al.; "Diphenylethanediamine (DPEDA) Derivatives as Chiral Selectors: IV. A Comparison of 3,5-Dinitrobenzoylated (S,S)- and (S,R)-Dpeda-Derived Chiral Stationary Phases With Pirkle's Standard (R)-Phenylglycine-Derived Phase in Nonna! Phase HPLC" Chirality 6:116-128 (1994).

Welch; "Evolution of Chiral Stationary Phase Design in the Pirkle Laboratories"; Journal of Chromatography A, 666 (1994) 3-26.

Kosjek, et al.; "Immobilization of Difunctional Building Blocks on Hydroxysuccinimide Activated Silica: Versatile in Situ Preparation of Chiral Stationary Phases" Chirality 13:657-667 (2001).

International Search Report and Written Opinion of the International Searching Authority; PCT/HR2009/000006; Jun. 4, 2009; 13 pages.

Kontrec, et al.; "Novel Chiral Stationary Phases Comprising 2,4-(or 2,6)-Diamino-5,6-(or 2,5)-dichlorobenzene-1,3-dicarbonitrile and 1-Acyl (1R,2R)diaminocyclohexane"; Enantiomer, vol. 5; pp. 333-344; 2000.

Adams, et al.; "Pharmacological Differences between the optical isomers of ibuprofen: evidence for metabolic Inversion of the (−)-isomer"; Communications, J. Pharm. Pharmac., 1976; 28; 256; 2 pages.

Kontrec, et al; "Solid-Phase Synthesis of Chiral Stationary Phases Based on 2,4,5,6-Tetrachloro-1,3-dicyanobenzene Derivatives Spaced from N-3,5-Dinitrobenzoyl Alpha-Amino Acids: Comparative Study of Their Resolution Efficacy"; Chirality 13:294-301; (2001).

* cited by examiner

CHIRAL STATIONARY PHASES FOR CHROMATOGRAPHY BASED ON AROMATIC ALLYL AMINES

CROSS-REFERENCE TO RELATED APPLICATIONS

The present application is a continuation of pending International Patent Application PCT/HR2009/000006 filed on Feb. 26, 2009 which designates the United States and claims priority from Croation Patent Application P20080102A filed on Mar. 7, 2008, the content of which is incorporated herein by reference.

FIELD OF THE INVENTION

This invention relates to the preparation of novel chiral stationary phases where the chiral selectors are covalently bound to a solid support. Materials obtained in such a manner enable enantioselection during the process of racemate separation or partially enantiomer enriched compounds. As such, the invention is classified according to international patent classification in group C07D—organic chemistry—heterocyclic compounds.

BACKGROUND OF THE INVENTION

Enantiomer separation by liquid chromatography is based on the selective enantiomer interaction with the chiral stationary phase (CSP). The direct enantiomer separation method, in its basic embodiment, enables interaction of the racemic mixture or mixture of enantiomers enriched on one of the enantiomers, with the chiral stationary phase that is usually used in the chromatographic column.

BRIEF DESCRIPTION OF THE DRAWINGS

This invention is represented in the Figures below that show.

DETAILED DESCRIPTION OF THE INVENTION

This invention relates to chiral stationary phases for liquid chromatography useful to separate many racemic or enantiomerically enriched mixtures, represented by structure CSP I:

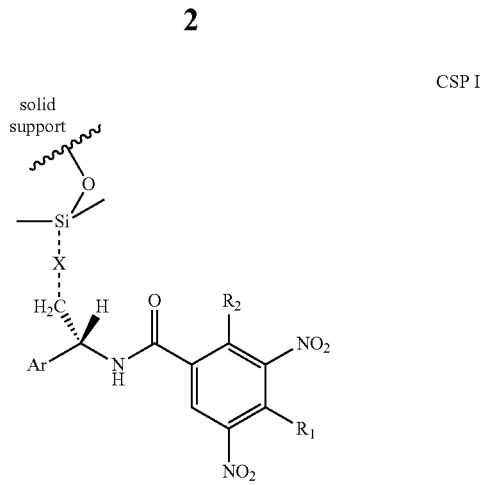

where $R_1$ and $R_2$ indicate hydrogen atom or methyl group, Ar indicates a group selected among phenyl, 3,5-dimetylphenyl, 1-naphthyl or 9-antryl, and X indicates $(-CH_2-)_n$, where n=0, 1, or 2, as a linker, where the linker group (linker) is covalently bound to the solid support for chromatography. Preferably, X indicates $(-CH_2-)_n$, where n=1, as a linker. The (S)-absolute configuration of the selector is selected by chance, and may also be (R)-configuration.

The solid support is made of a material suitable for use in conditions of chromatographic separation, and preferably of an inorganic nature. Solid supports for chromatography contain preferably hydroxyl groups (or otherwise hydroxylated groups) which are capable of forming covalent bond with appropriate functional groups, forming a functional solid support. Thus, the solid support is bound to molecule having the formula CSP I by covalent bond that includes one of the hydroxylated/oxygenated groups of the solid support. Examples of solid supports are silica gel, aluminum oxide, kaoline, titanium oxides, magnesium oxides, silicates and synthetic polymers.

Further subject of this invention is the method for the preparation of chiral stationary phases of formula CSP I. In its most basic embodiment this invention includes the following phases:

racemic aromatic allyl amine synthesis;

chiral aromatic amine enantiomer resolution by enzymes or by diastereoisomeric salts with an optically pure acid that can be recycled;

formation of covalent bond between the linker and the solid support.

Figure 1:
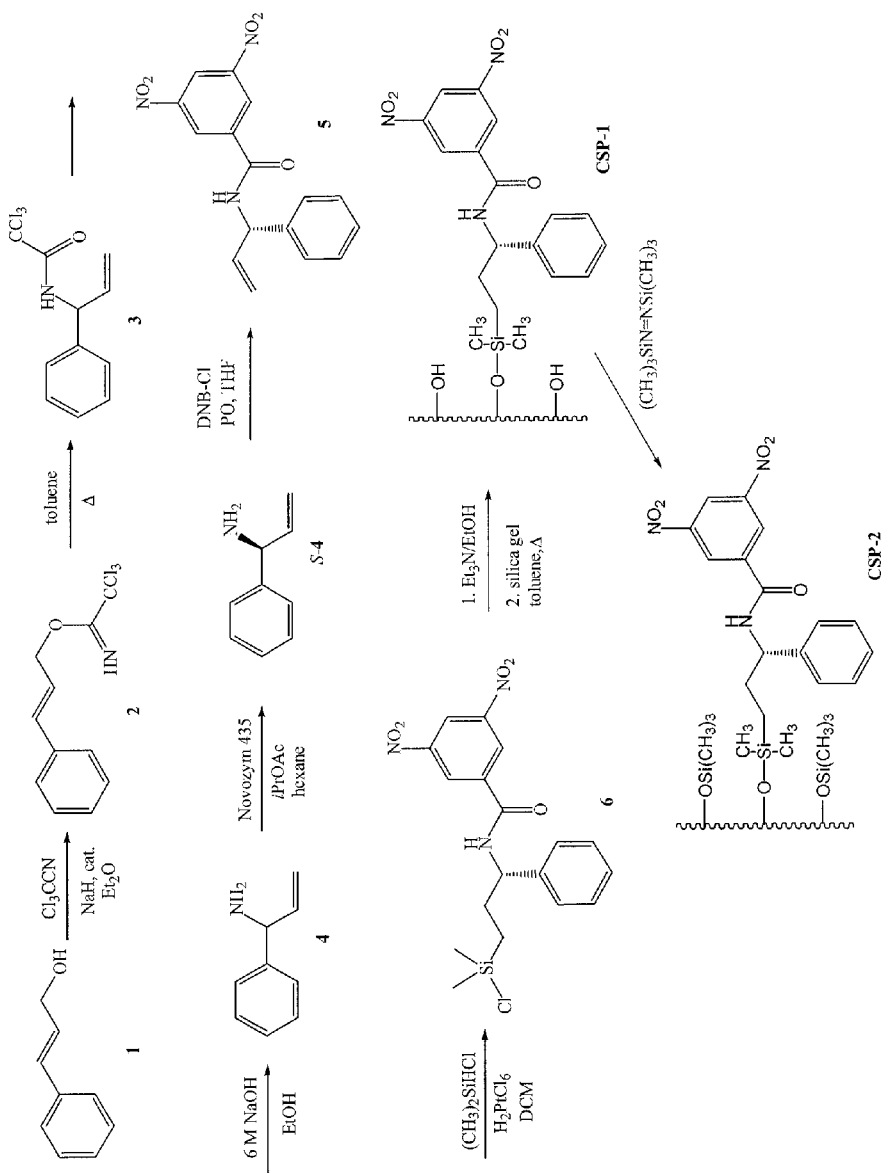
FIG. 1. Synthetic pathway to CSP-1 and CSP-2
Figure 2:
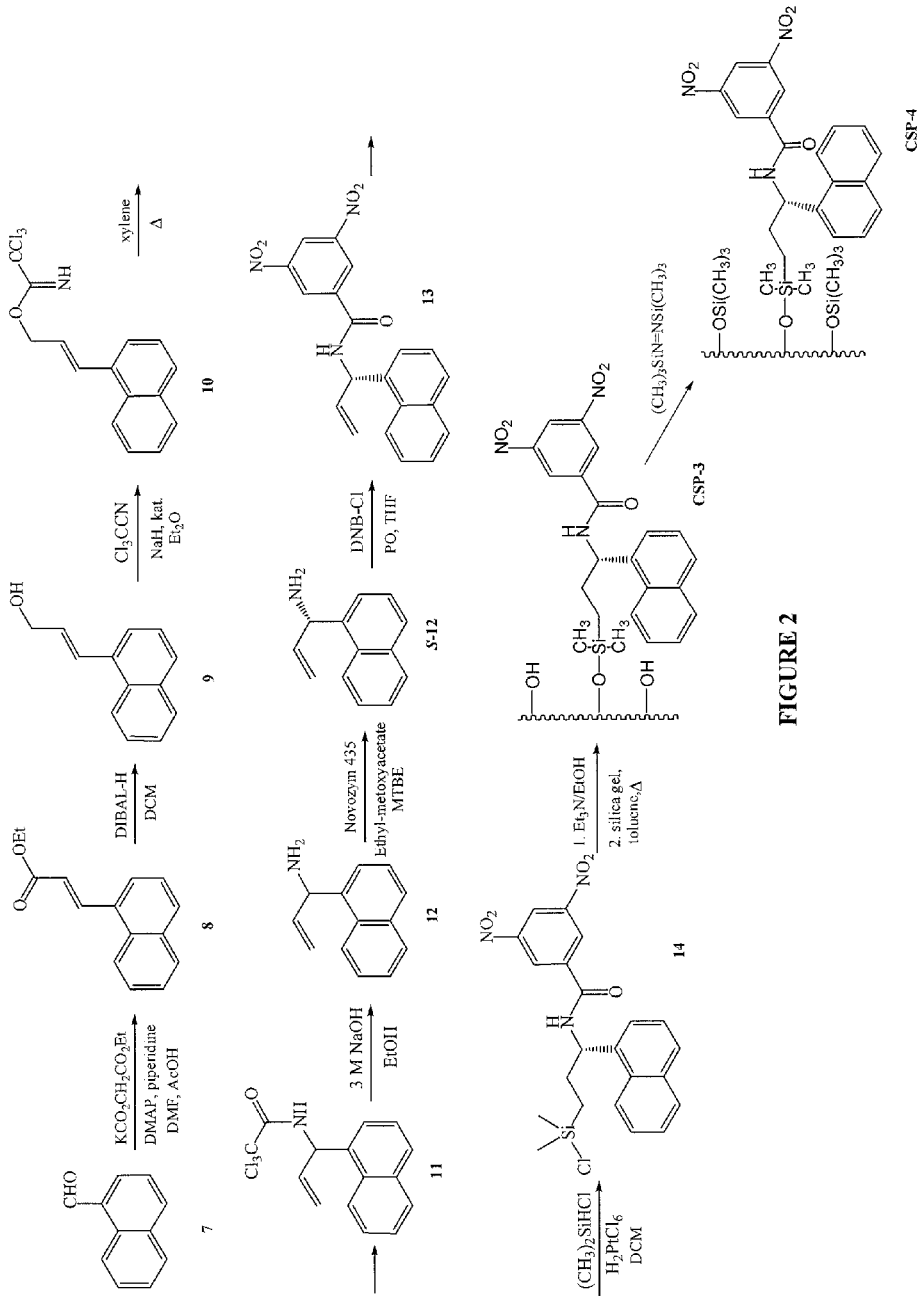
FIG. 2. Synthetic pathway to CSP-3 and CSP-4

FIGS. 1 and 2 represent possible preparation pathways of some of the chiral stationary phases, claimed herewith.

The described stationary phases enable separation of different commercial and industrial racemic mixtures. A further aspect of this invention is the use of chiral stationary phases for enantioseparation by means of chromatography, and especially their use in liquid chromatography column preparation.

This invention enables analytical and preparative separation of enantiomers with various chemical structures. Furthermore, the mentioned enantioseparation enables precise determination of the enantiomer mixture composition, produced for example by asymmetric (enantioselective) synthesis.

The process of enantioseparation includes different interactions between the chiral selector and certain enantiomers. Generally, the process is based on non-covalent interactions between chiral selectors and enantiomers, combination of hydrogen interactions, π-π interactions, hydrophobic and van der Waals interactions (C. Allenmark, "Chromatographic Enantioseparation Methods and Application", 2nd. ed., New York, Ellis Horwood, 1991). It has been observed that the combination of π-donor and π-acceptor aromatic systems in the chiral selector is crucial for enantioseparation of a wide spectrum of racemic analytes (C. J. Welch, *J. Chromatogr. A*, 1994, 666, 3-26; M. H. Huyn, Y. D. Kim, S. C. Han, J. B. Lee, *J. High Resol. Chromatogr.* 1998, 21, 464-470). The branching unit, i.e., the part of the chiral selector that bounds the linker with the chiral unit in CSP, can also act as a π-donor or π-acceptor component in CSP (D. Kontrec, V. Vinković, A. Lesac, V. Šunjić, A. Aced, *Enantiomer,* 2001, 5, 333-34; D. Kontrec, A. Abbatangelo, V. Vinković, V. Šunjić, *Chirality,* 2001, 13, 294-301).

A basic characteristic of these CSPs is their specific rigid and simple structure. From the silica gel surface toward the elution medium 3,5-dinitrobenzoyl group is directed, which is extremely poor with π-electrons and thus easily generates π-π interactions. A second aromatic group, rich with electrons, is placed behind the previous one, creating a shield in front of the silica gel surface, which lowers the non-productive achiral interactions with the polar silica gel groups. Unlike most contemporary chiral stationary phases, the phases described herein do not contain an additional amide bond on the linker toward the silica gel. In this manner, the influence of achiral interactions is further decreased and thus, the chiral stationary phases of this invention offer unambiguous results in chiral recognition.

This invention solves the problem of ineffective or less effective separation of certain groups of racemic mixtures commonly obtained by most commercially available brush-like chiral stationary phases, due to the specific chemical structure of the new chiral selectors, which are the subject of this invention. Specifically, this invention solves the problem of enantiomer separation of α-aryl propanoic acids, i.e. profens, substances from the group of non-steroidal anti-inflammatory drugs. These are chiral compounds known to be much more active when in (S)-enantiomer form; for example, it has been measured that (S)-naproxen possesses 28-fold stronger anti-inflammatory activity than the appropriate (R)-enantiomer (S. S. Adams, P. Bresloff, C. G. Mason, *J. Pharm. Pharmacol.* 1976, 28, 256). Furthermore, this invention especially solves the problem of poor or ineffective racemic mixture separation on columns that were subject matter of earlier patent applications (V. Šunjić, D. Kontrec, V. Vinković, WO 00/00464, 2000; D. Kontrec, V. Vinković, V. Šunjić, P. Mariotti, L. Navarini, WO 02/070124 A1, 2002), where the chiral stationary phases were composed of more complex chiral selectors. Due to their more complex structure, these stationary phases are less universal, unlike the chiral stationary phases that are subject matter of this invention. They are composed of less complex chiral selectors, but with completely defined geometry, due to which they can create complexes with analytes having different structures and thus separate their enantiomers.

Structures of chiral stationary phases described in this invention are most similar to the Whelk-O1 chiral phase developed by Pirkle et. al. (W. H. Pirkle, C. J. Welch, B. R. Lamm, WO 93/06080, 1993; W. H. Pirkle, C. J. Welch, B. R. Lamm, WO 96/39377, 1996) and commercially available through Regis Technologies, Inc. (Morton Grove, Ill., USA). Whelk-O1 is the most universal brush-like type chiral stationary phase described so far and commercially the most successful.

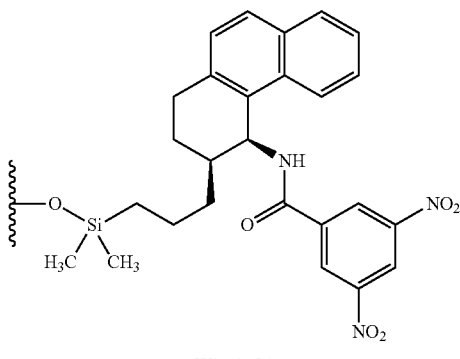

Whelk-O1

However, the chiral stationary phases described in this invention have several crucial advantages in respect to the Whelk-O1 phase. The first advantage relates to the chiral selector structure, which in Whelk-O1 phase is derived from tetrahydrophenanthrene and thus strengthened by an additional ring. This makes the geometry of the selector strongly rigid, but also less adaptable to interact with the analytes. Chiral stationary phases of type CSP I described in this invention do not contain such additional rigidness and despite their rigid geometry are able to partially adapt the chiral cavity and interact with structurally different analytes. This especially relates to selectors derived from amine comprising a small aromatic group, while the CSP I preparation method allows adaptability of the aromatic group. Further advantage of the chiral stationary phases of this invention relates to their preparation method. To obtain an enantiomerically pure chiral selector for Whelk-O1, it is necessary to separate selector enantiomers prior to their linkage to the silica gel by chiral chromatography. Since the selector contains the 3,5-dinitrobenzoyl group, it can easily be separated using π-donor chiral stationary phases. The problem is its solubility, which is very low and, therefore, the chromatographic productivity is also very low. In the case of CSP I in this invention, certain enantiomers of aromatic allyl amines are separated using diastereoisomer salts or enzymes, preferably with enzymes that are used in industry on a large scale and are easily available at low prices. This method can be performed on considerably larger scales and, thus, the chiral selector productivity and availability are significantly more advantageous.

Specific examples of chiral selectors and chiral stationary phases preparation and racemic enantioseparation on new stationary phases, which are subject matter of this invention, are presented in the experimental part. Special attention is payed to racemic separations of therapeutic and commercial interest, such as benzodiazepine and binaphtol derivatives and anti-inflammatory drugs from the profen group.

The following examples are intended to describe this invention better and are limiting in no case.

Examples of Chiral Selectors and Chiral Stationary Phase Preparation

EXAMPLE 1

Cinnamolic ester of 2,2,2-trichloracetimid acid (2

240 mg (7.45 mmol) of sodium hydride (80% dispersion in mineral oil) was dispersed in an inert atmosphere in 5 ml of dry diethyl-ether. A solution of cinnamol (1, 10 g, 74.53 mmol) in dry diethyl-ether (10 ml) was added drop-wise and stirred for 15 min at 20° C. The reaction mixture was cooled to −10° C. and trichloroacetonitril (8.2 ml, 81.98 mmol) was added drop-wise, not allowing the reaction temperature to increase over 0° C. It was further stirred for 45 min at −10° C., and then 20 h at 20° C. The light-yellow reaction mixture was evaporated to give an oil crude product that was dispersed in a hexane (111 ml) and methanol (0.3 ml) mixture. The obtained residue was separated by filtration and washed with diethyl-ether (2×10 ml). The filtrate was evaporated to give 20.818 g (97%) of yellow oil. According to $^1$H NMR spectrum and HPLC analysis, compound 2 was satisfactorily pure for further reaction; $^1$H NMR (CDCl$_3$) δ: 4.97 (d, 2H, J=6.4 Hz, CH$_2$O), 6.40 (td, 1H, J=6.0 Hz, J=16.0 Hz, CHCH$_2$), 6.75 (d, 1H, J=16.0 Hz, PhCHCH), 7.25-7.29 (1H, m, ArH), 7.31-7.35 (2H, m, ArH), 7.40-7.44 (2H, m, ArH), 8.40 (s, 1H, NH) ppm; $^{13}$C NMR (CDCl$_3$) δ: 69.80 (CH$_2$O), 95.6 (CCl$_3$), 126.74 (C$_2$ and C$_6$Ph), 128.21 (C$_4$Ph), 128.66 (C$_3$ and C$_5$Ph), 136.14 (C$_1$Ph), 162.56 (CNH) ppm.

EXAMPLE 2

N-(1-Phenylallyl)-2,2,2-trichloroacetamide (3)

In an inert atmosphere, compound 2 (20 g, 72.0 mmol) was refluxed for 48 h in 450 ml of dry toluene. After cooling, the dark mixture was filtered through a short silica gel column (2×4 cm) and washed with 100 ml of toluene. Filtrates were combined and evaporated, resulting in a red-yellow oil that slowly crystallizes at 4° C. The crude product was purified by chromatography on a silica gel column with CH$_2$Cl$_2$/hexane=5:1 as the mobile phase. The yield was 14.2 g (71%) of a light yellow solid that melts at room temperature; $^1$H NMR (CDCl$_3$) δ: 5.32 (1H, d, J=17.2 Hz, CH$_2$CH), 5.36 (1H, d, J=10.6 Hz, CH$_2$CH), 5.57 (1H, m, CHNH), 6.06 (1H, m, CHCH$_2$), 6.89 (1H, bs, NH), 7.31-7.37 (3H, ArH), 7.38-7.42 (3H, ArH) ppm; $^{13}$C NMR (CDCl$_3$) δ: 59.10 (CNH), 101.0 (CCl$_3$), 115.3 (CH$_2$), 126.74 (C$_2$ and C$_6$Ph), 128.21 (C$_4$Ph), 128.6 (C$_3$ and C$_5$Ph), 135.2 (CCH$_2$), 136.14 (C$_1$Ph), 162.56 (COCCl$_3$) ppm.

EXAMPLE 3

1-Phenylallylamine (4)

Amid 3 (13.9 g, 49.9 mmol), prepared as described in Example 2, was dissolved in 267 ml of distillated ethanol and 240 ml of 6 M aqueous solution of NaOH was added to the solution. The reaction mixture was stirred at 20° C. for 72 h, evaporated to aqueous remain which was acidified with 5 M HCl to pH=2. It was extracted twice with 100 ml dichloromethane. The aqueous layer was alkalified with sodium carbonate to pH=8 and extracted three times with 100 ml diethyl-ether. Organic layers were combined and dried over anhydrous sodium sulphate. By filtration and evaporation, the yield was 3.19 g (48%) of yellow oil; $^1$H NMR (CDCl$_3$) δ: 1.69 (2H, bs, NH$_2$), 4.52 (1H, d, J=5.8 Hz, CHNH$_2$), 5.11 (1H, d, J=10.2 Hz, CHCH$_2$), 5.24 (1H, d, J=17.2 Hz, CHCH$_2$), 6.03 (1H, m, CHCH$_2$), 7.33-7.35 (5H, m, ArH) ppm; $^{13}$C NMR (CDCl$_3$) δ: 55.9 (CNH), 114.8 (CH$_2$), 126.3 (CPh), 127.4 (2×CPh), 128.2 (2×CPh), 134.7 (CCH$_2$) ppm.

EXAMPLE 4

(S)-1-Phenylallylamine (S-4)

Amine 4 (200 mg, 1.5 mmol) was dissolved in 20 ml of isopropyl-acetate and 3 ml of hexane and 4.0 g of Novozym 435 was added. The mixture was stirred for 48 h at 30° C. The reaction progress was followed by HPLC analysis on the Chiralcel OD HPLC column (250×4.6 mm) with hexane/isopropanol/diethylamine=95/5/0.2 (1 ml/min, 254 nm, $t_{R(R)}$=7.1 min, $t_{R(S)}$=9.1 min) as the mobile phase. After the reaction completion, the enzyme was separated by filtration and the filtrate was evaporated to oil residue. It was dispersed in 10 ml of 1 M HCl and extracted twice with 10 ml of dichloromethane. The aqueous layer was alkalified with a solid sodium carbonate to pH=8 and extracted three times with 15 ml diethyl-ether. Organic layers were combined and dried over anhydrous sodium sulphate, filtered and evaporated to give 94 mg (94%) of yellow oil. According to HPLC analysis ee>99%. $[\alpha]_D^{25}$=−10.2 (c=1 M, CHCl$_3$).

EXAMPLE 5

(S)-N-(1-Phenylallyl)-3,5-dinitrobenzamide (5)

3,5-Dinitrobenzoyl chloride (190 mg, 0.83 mmol) and amine S-4 (100 mg, 0.75 mmol) were dissolved in an inert atmosphere in 15 ml of dry tetrahydrofuran (THF). The yellow solution was stirred for 10 min at 20° C., and cooled in ice bath at 4° C. 1 ml (14.3 mmol) of propylene oxide was added and stirred at a lowered temperature for 45 min, and then for 20 h at 20° C. The reaction mixture was evaporated to a pale-yellow amorphous remain which was recrystallized from 6 ml of methanol. White needle crystals in amount of 140 mg were yielded. The filtrate recrystallization was repeated twice. The total mass of isolated crystals was 200 mg (81%). $[\alpha]_D^{25}$=−21 (c=0.03 M, THF); $^1$H NMR (CDCl$_3$) δ: 5.25-5.33 (2H, m, CH$_2$CH), 5.80 (1H, bd, J=6.3 Hz, ArCHNH), 6.19 (1H, m, CHCH$_2$), 7.24-7.43 (5H, m, ArH), 9.08 (2H, d, J=2.0 Hz, Ar(NO$_2$)$_2$o-H), 9.12 (1H, t, J=2.0 Hz, Ar(NO$_2$)$_2$p-H) ppm; $^{13}$C NMR (CDCl$_3$) δ: 56.7 (PhCNH), 115.9 (CH$_2$), 120.7 (p-CAr(NO$_2$)$_2$), 127.0 (p-CPh), 127.3 (2×o-CPh), 128.3 (2× m-CPh), 136.7 (CHCH$_2$), 137.4 (CAr(NO$_2$)$_2$), 140.4 (CAr), 148.7 (2× CNO$_2$), 152.7 (CO) ppm.

EXAMPLE 6

(S)-N-[1-Phenyl-3-(chlorodimethylsilyl)-propyl]-3, 5-dinitrobenzamide (6)

1 g (3.06 mmol) of amide 5 was dispersed in an inert atmosphere in 10 ml of dry dichloromethane. 12 mg of H$_2$PtCl$_6$.xH$_2$O was dispersed in 0.25 ml isopropanol and the obtained brown suspension was added to the reaction mixture. Afterwards, 10 ml of dimethylchlorosilane (92 mmol) was added and the reaction mixture was stirred on a reflux temperature for six hours. The transparent yellow solution was evaporated to paste remain which was dissolved in 5 ml of dry dichloromethane and again evaporated until dry.

EXAMPLE 7

Chiral Stationary Phase CSP-1

Compound 6 from Example 6 was dissolved in 9 ml of dry dichloromethane and a mixture of triethylamine (5 ml) and absolute ethanol (5 ml) were gradually added drop-wise into reaction mixture. The mixture was than stirred at 20° C. for half an hour and evaporated to an oil residue. The product was purified onto a silica gel column with dichloromethane:methanol=100:1 as a mobile phase. Fraction evaporation yields a yellow-green paste dissolved in 10 ml of dry toluene and added to a silica gel suspension (3.0 g; particles size 5 μm) in 100 ml of dry toluene in a Dean-Stark apparatus. The obtained suspension was stirred at reflux temperature for 24 h and filtered over a G-4 funnel, and the solid product was washed with 50 ml of toluene, 50 ml of methanol and 50 ml of propan-2-ol. After drying at 60° C. for 6 h, the yield was 3.05 g CSP-1. Elemental analysis: C 5.19%, H 1.22% and N 1.01%), showed that the stationary phase was composed of 0.24 mmol/g of bounded chiral selector.

EXAMPLE 8

Chiral Stationary Phase CSP-2

2.7 g CSP-1, prepared as described in Example 7, was dispersed in 18 ml of dry dichloromethane in an inert atmosphere and 2 ml (9.47 mmol) of hexamethyldisilazane was added. It was stirred for 24 h at 20° C. and the suspension was filtered over a G-4 funnel and the obtained product was washed with 20 ml dichloromethane, methanol and isopropanol. After drying at 60° C. for 6 h, the yield was 2.77 g of CSP-2.

EXAMPLE 9

(2E)-Ethyl ester of 3-(napht-1-yl)acrylic acid (8)

Pyrid-4-yl-dimethylamine (780 mg; 6.4 mmol) was dissolved in 60 ml of N,N-dimethylformamide. Than, 8.17 g (48 mmol) of potassium monoethyl-malonate and 4.3 ml (32 mmol) of 1-naphthylaldehyde was added into the solution. The suspension was cooled in a ice bath and 2.8 ml (48 mmol) of acetic acid, and 0.64 ml (6.4 mmol) of piperidine was added drop wise to the reaction mixture. It was stirred for 48 h at 20° C., then heated to 60° C. and stirred for 96 h. 100 ml of diethyl-ether and 50 ml of water was added and layers were separated. The organic layer was washed with 50 ml of a saturated aqueous solution of ammonium chloride, 50 ml of water and 50 ml of a saturated aqueous solution of sodium hydrogen carbonate, and then dried over anhydrous sodium sulphate. Filtration and evaporation yields 7.023 g (97%) of yellow oil. After HPLC analysis and $^1$H NMR spectrum, the obtained product was sufficiently pure for the further reaction step; $^1$H NMR (CDCl$_3$) δ: 1.38 (t, 3H, J=7.1 Hz, CH$_3$CH$_2$O), 4.32 (q, 2H, J=7.1 Hz, CH$_3$CH$_2$O), 6.53 (d, 1H, J=15.8 Hz, ArCHCH), 7.25-7.29 (1H, m, ArH), 7.43-8.22 (7H, m, ArH), 8.52 (d, 1H, ArCHCH) ppm.

EXAMPLE 10

(2E)-3-(Napht-1-yl)-prop-2-en-1-ol (9)

In an inert atmosphere, 3.5 g (15.5 mmol) of ester 8 was dissolved in 70 ml of dry dichloromethane and the yellow solution was cooled to −20° C. In this solution, 32 ml (32.2 mmol) of 1M solution of diisobutylaluminium hydride (DIBAL-H) in toluene was added gradually and drop-wise. It was stirred over three hours from −20° C. to −10° C. and then for another hour at 0° C. In the obtained solution 30 ml of ethanol and 50 ml of saturated aqueous solution of potassium sodium tartarate (Rochelle salt) were added. Layers were separated, and the aqueous layer was washed with dichloromethane (3×50 ml). The organic layers were combined and dried over anhydrous sodium sulphate. Filtration and evaporation yields a red-yellow oil which was purified by chromatography over a silica gel column with hexane:ethyl-acetate=2:1 as the mobile phase. Yields 2.6 g (91%) of the oil product; $^1$H NMR (CDCl$_3$) δ: 1.68 (bs, 1H, OH), 4.42 (d, 2H, J=5.4 Hz, CHCH$_2$OH), 6.38 (dt, 1H, J=15.8 Hz, J=5.4 Hz, CHCH$_2$), 7.37 (d, 1H, J=15.8 Hz), 7.42-8.15 (7H, m, ArH) ppm; $^{13}$C NMR (CDCl$_3$) δ: 63.44 (CH$_2$OH); 123.26 (CH); 123.44 (CH); 125.13 (CH); 125.31 (CH); 125.57 (CH); 127.55 (CH); 127.71 (CH); 128.05 (CH); 130.68 (C); 131.31 (CH); 133.12 (C); 133.97 (C) ppm.

EXAMPLE 11

(2E)-3-(Napht-1-yl)-allyl ester of 2,2,2-trichloroacetimid acid (10)

Sodium hydride (60% dispersion in mineral oil, 51 mg, 1.28 mmol) was dispersed in an inert atmosphere in 10 ml of dry diethyl-ether. A solution of alcohol 9 (2.6 g, 14.09 mmol) in dry diethyl-ether (20 ml) was added and was stirred for 15 min at 20° C. The reaction mixture was cooled to −10° C. and trichloroacetonitril (1.5 ml, 14.1 mmol) was added drop-wise over 5 min. Upon completion, it was stirred for 15 min at −10° C., heated to room temperature and stirred for 48 h at 20° C. The yellow reaction mixture was evaporated to an oil residue that was dispersed in a hexane (5 ml) and methanol (30 μl) mixture. The obtained white residue was separated by filtration and washed with diethyl-ether (2×10 ml). The filtrate was evaporated, yielding 4.315 g (93%) of yellow oil. According to $^1$H NMR spectrum and HPLC analysis, compound 10 was satisfactorily pure for further reaction; $^1$H NMR (CDCl$_3$) δ: 5.09 (dd, 2H, J=6.1 Hz, J=1.5 Hz, CHCH$_2$O), 6.42 (dt, 1H, J=15.7 Hz, J=6.0 Hz, CHCH$_2$), 7.45 (d, 1H, J=15.7 Hz), 7.46-8.13 (7H, m, ArH), 8.41 (bs, 1H, NH) ppm; $^{13}$C NMR (CDCl$_3$) δ: 69.71 (CH$_2$OH); 123.65 (CH); 124.15 (CH); 125.51 (CH); 125.58 (CH); 125.88 (CH); 126.24 (CH); 128.46 (CH); 128.58 (CH); 131.50 (CH); 133.56 (C); 133.94 (C); 162.56 (CNH) ppm.

EXAMPLE 12

N-[1-(Napht-1-yl)-allyl]-2,2,2-trichloracetamide (11)

4.3 g (13.1 mmol) of compound 10 was dissolved in an inert atmosphere in 50 ml of dry xylene and refluxed for 22 h. The resulting solution was filtered over a short silica gel column and washed with 25 ml of toluene and 25 ml of dichloromethane. The filtrate was evaporated to an oil residue which was purified by chromatography over a silica gel column with hexane:dichloromethane=1:1 as the mobile phase. 3.01 g (70%) of white residue was yielded, m.p.=105-106° C.; $^1$H NMR (CDCl$_3$) δ: 5.36-5.49 (2H, m, J=17.2 Hz, CH$_2$CH), 6.17-6.30 (1H, m, CHCH$_2$), 6.31-6.38 (1H, m, CHAr), 6.88 (1H, d, J=6.4 Hz, NH), 7.45-7.61 (4H, m, ArH), 7.84-7.93 (m, 2H, ArH), 8.02 (d, 1H, J=8.2 Hz, ArH) ppm; $^{13}$C NMR (CDCl$_3$) δ: 53.27 (CCNH); 105.80 (CCl$_3$); 116.83 (CH$_2$); 123.03 (CH); 125.20 (CH); 125.25 (CH); 126.26 (CH); 127.09 (CH); 129.00 (CH); 129.48 (CH); 131.12 (C); 134.26 (C); 135.35 (CH) ppm.

EXAMPLE 12

1-(Napht-1-yl)-allylamine (12)

Amide 11 (3.0 g, 9.1 mmol) was dissolved in 50 ml of distilled ethanol and 50 ml of 3 M aqueous solution of NaOH was added. All was stirred at 20° C. for 24 h and evaporated to aqueous residue and 32 ml of 5 M HCl was added. It was extracted twice with 40 ml of dichloromethane. The aqueous layer was alkalified with sodium carbonate to pH=8 and extracted three times with 50 ml of diethyl-ether. Organic layers were combined and dried over anhydrous sodium sulphate. Filtration and evaporation yields 1.20 g (72%) of yellow oil; $^1$H NMR (CDCl$_3$) δ: 1.72 (2H, bs, NH$_2$), 5.18-5.24 (1H, m, CH$_2$), 5.30-5.38 (1H+1H, m, CHCH$_2$+ArCHNH$_2$), 6.15-6.27 (1H, m, CHCH$_2$), 7.42-7.60 (4H, m, ArH), 7.74-7.78 (m, 1H, ArH), 7.84-7.89 (m, 1H, ArH), 8.20 (d, 1H, J=8.3 Hz, ArH) ppm; $^{13}$C NMR (CDCl$_3$) δ: 53.92 (CNH$_2$), 114.28 (CH$_2$), 123.41 (CH), 123.51 (CH), 125.55 (CH), 125.56 (CH), 126.05 (CH), 127.80 (CH), 128.92 (CH), 131.40 (C), 134.00 (C), 141.71 (CH) ppm.

EXAMPLE 13

(S)-1-(Napht-1-yl)-allylamine (S-12)

Amine 12 (600 mg, 3.3 mmol) was dissolved in 40 ml of methyl-tert-butyl-ether. 1 ml of ethyl-metoxyacetate and 5.0 g of Novozym 435 were added, and all was stirred for 120 h on 30° C. Reaction was followed by HPLC analysis on the Chiralcel OD column (250×4.6 mm) with hexane:t-BuOH:dimethylamine=92:8:0.2 (1 ml/min, 254 nm, $t_{R(S)}$=15.31 min, $t_{R(R)}$=18.28 min) as the mobile phase. The enzyme was separated from the reaction mixture by filtration and the filtrate was evaporated to oil remain which was dispersed in 10 ml of 1 M HCl and extracted twice with 20 ml of dichloromethane. The aqueous layer was alkalified with a solid sodium carbonate to pH=8 and extracted three times with 20 ml of diethyl-ether. Organic layers were combined and dried over anhydrous sodium sulphate. After filtration and solvent removal, S-12 as yellow oil (267 mg; 89%) was yielded. According to HPLC analysis ee>99%. $[\alpha]_D^{25}$=−46 (c=0.05 M, CHCl$_3$).

EXAMPLE 14

(S)-N-[1-(Napht-1-yl)-allyl]-3,5-dinitrobenzamide (13)

3,5-Dinitrobenzoyl chloride (370 mg, 1.6 mmol) and amine S-12 (267 mg, 1.5 mmol) were dissolved in an inert atmosphere in 10 ml of dry tetrahydrofurane (THF). The yellow solution was stirred for 10 min at 20° C., and then cooled in a ice bath at 4° C. Propylene oxide (21.5 mmol) in amount of 1.5 ml of was added and all was stirred at a lower temperature for 45 min, and then for 20 h at 20° C. The reaction mixture was evaporated to a pale-yellow amorphous remain which was recrystallized from 12 ml of methanol. 423 mg of white needle crystals were yielded. The filtrate was evaporated to dryness and once again recrystallized with 5 ml of methanol. 72 mg of white crystals were yielded. Total crystal mass was 495 mg (87%). $[\alpha]_D^{25}$=+38 (c=0.03 M, acetone); m.p.=201-203° C.; $^1$H NMR (CDCl$_3$) δ: 5.28 (1H, dd, J=17.2 Hz, J=1.8 Hz, CH$_2$CH), 5.39 (1H, dd, J=10.4 Hz, J=1.8 Hz, CH$_2$CH), 6.16-6.28 (1H, m, CHCH$_2$), 6.47-6.51 (1H, m, NH), 7.39-7.53 (4H, m, ArH), 7.76-7.85 (m, 2H, ArH), 7.95-8.0 (m, 1H, ArH), 8.99 (2H, d, J=2.0 Hz, Ar(NO$_2$)$_2$o-H), 9.04 (1H, t, J=2.0 Hz, Ar(NO$_2$)$_2$p-H) ppm; $^{13}$C NMR (CDCl$_3$) δ: 52.0 (ArCNH), 116.61 (CH$_2$), 120.91 (CH), 123.10 (CH), 125.11 (CH), 125.13 (CH), 125.48 (CH), 126.14 (CH), 126.93 (CH), 127.58 (CH), 128.81 (CH), 128.93 (CH), 131.06 (C), 133.81 (C), 135.23 (C), 136.01 (CH), 137.25 (C), 148.29 (C), 162.03 (CO) ppm.

EXAMPLE 15

(S)-N-[1-(Napht-1-yl)-3-(chlorodimethylsilyl)-propyl]-3,5-dinitrobenzamide (14)

1 g (2.65 mmol) of amide 7 was dispersed in an inert atmosphere in 10 ml of dry dichloromethane. 20 mg of H$_2$PtCl$_6$.xH$_2$O was dispersed in 0.30 ml of isopropanol and the resulting brown suspension was added to the reaction mixture. Then 10 ml (92 mmol) of dimethylchlorosilane was added and the mixture was stirred to reflux temperature for six hours. The transparent brown solution was evaporated to paste residue which was dissolved once again in 5 ml of dry dichloromethane, and all was once again evaporated until dry.

EXAMPLE 16

Chiral Stationary Phase CSP-3

Compound 14 was dissolved in 8 ml of dry dichloromethane and progressively a mixture of triethylamine (5 ml) and absolute ethanol (5 ml) was added drop-wise. After that, the mixture was stirred for half an hour at 20° C. and evaporated to an oil remain. The remain was purified on a silica gel column with dichloromethane:methanol=100:1 as the mobile phase. The filtrate evaporation yields yellow paste. The resin was dissolved in 10 ml of dry toluene and added to a silica gel suspension (3.0 g; 5 μm) in 100 ml of dry toluene in the Dean-Stark apparatus. The suspension was stirred on reflux temperature for 24 h, filtered over a G-4 funnel and the product was evaporated with 50 ml of toluene, 2×50 ml of methanol and 50 ml of isopropanol. The product was then dried at 60° C. for 4 h, yielding 3.07 g of CSP-3. Elemental analysis: C 5.65%, H 1.42% and N 0.98%), shows that the stationary phase was composes of 0.23 mmol/g of bounded chiral selector.

EXAMPLE 17

Chiral Stationary Phase CSP-4

2.5 g of dried CSP-3, prepared as described in Example 16, was dispersed in 20 ml of dry dichloromethane in an inert atmosphere and 3 ml (14.2 mmol) of hexamethyldisilazane was added. All was stirred for 24 h at 20° C. and then the suspension was filtered through a G-4 funnel and washed with 20 ml of dichloromethane, methanol and isopropanol, separately. The product was dried at 60° C. for 4 h, yielding 2.62 g of CSP-4.

Examples of Racemate Separation on the Chiral Stationary Phases of this Invention

EXAMPLE 18

The General Procedure for Separation of Racemic Analytes on HPLC Columns Containing the Chiral Stationary Phase from this Invention HPLC measures were preformed on a Knauer HPLC Pump 64 apparatus (Knauer, Berlin, Germany) equipped with a 4-Port Knauer Degasser, a CD detector Jasco CD-2095 (Jasco, Tokyo, Japan), simultaneously detecting both UV and CD signals, an Interface Knauer, solvent saver VICI Jour Research Model 2909 (VICI Jour Research, Onsala, Sweden) and a UV detector Knauer Variable Wavelength Monitor. Detection was performed at 254 nm for both detectors. Chromatogram integrating was performed with the Chromatography Software Management System EUROCHROM 2000 for Windows, Version 1.65, software package (Knauer, Berlin, Germany).

HPLC column filling, purchased at Max Stevenson (Berlin, Germany), 250 mm×4.6 mm I.D. was performed with the suspension technique using the Knauer pneumatic pump.

Analytically pure and previously distillated n-hexane, propan-2-ol and dichloromethane (J. T. Baker) were used for chromatography and column loading. The dead volume ($t_0$) of HPLC column was determined by 1,3,5-tri-tert-butylbenzene. Analyte specimens were prepared by dissolving approx. 1 mg of racemic compound in 1 ml of propan-2-ol. 5 μl of freshly prepared solution was injected for analytical purposes.

Based on enantiomer retention times ($t_{R1}$ and $t_{R2}$), the following chromatography parameters were calculated: first, enantiomer retention factor $k_1=(t_1-t_0)/t_0$; second, enantiomer retention factor $k_2=(t_1-t_0)/t_0$; separation factor $\alpha=k_2/k_1$; and resolution factor $R_S=2(t_2-t_1)/(w_1+w_2)$, where w is the curve width at the chromatogram baseline obtained by drawing a tangent through inflection points of the chromatographic peak.

EXAMPLE 19

Enantiomer Separation on CSP-1 and CSP-2

Figure 3:
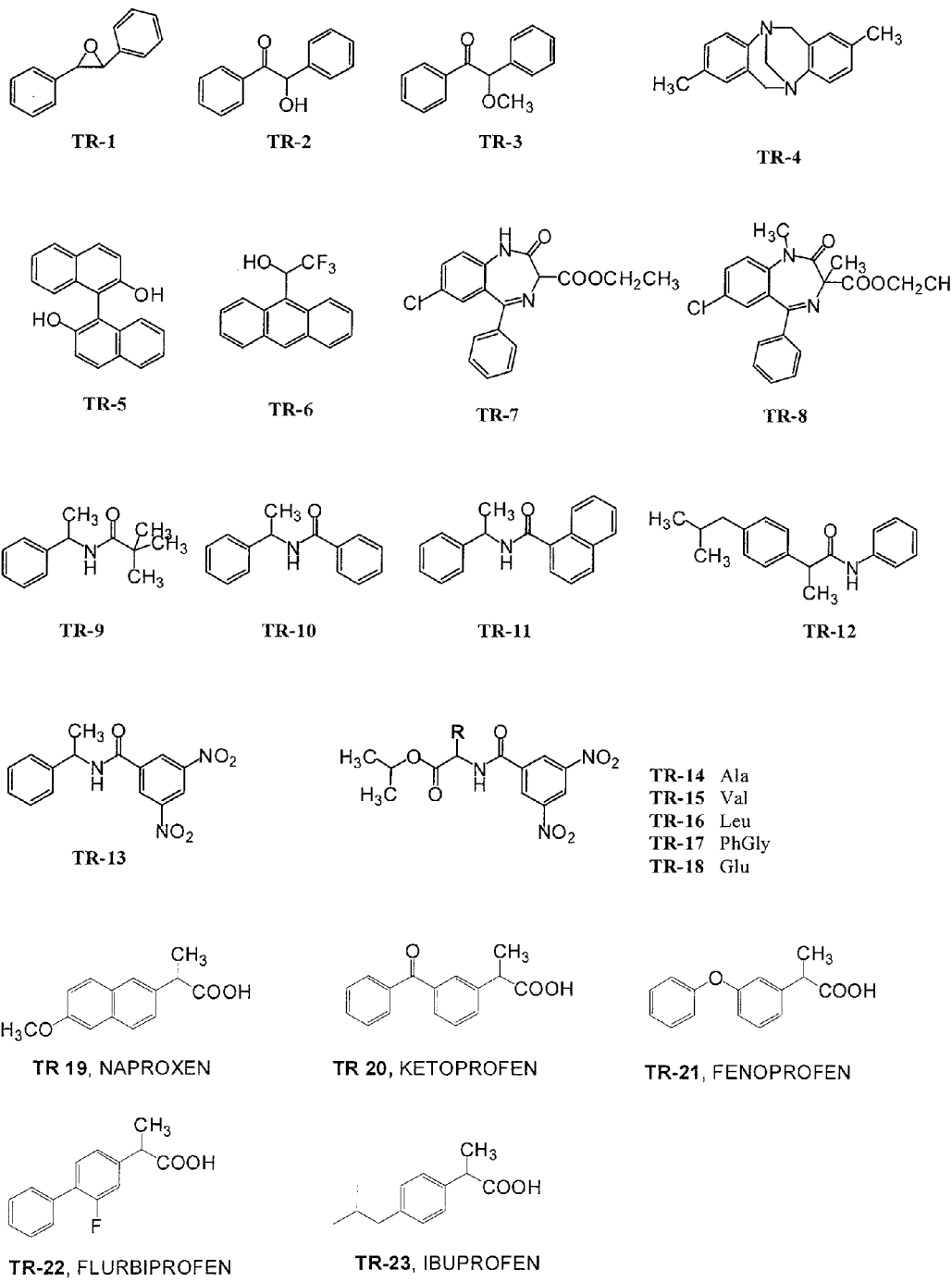
FIG. 3. Structure of the test racemates
Figure 4:
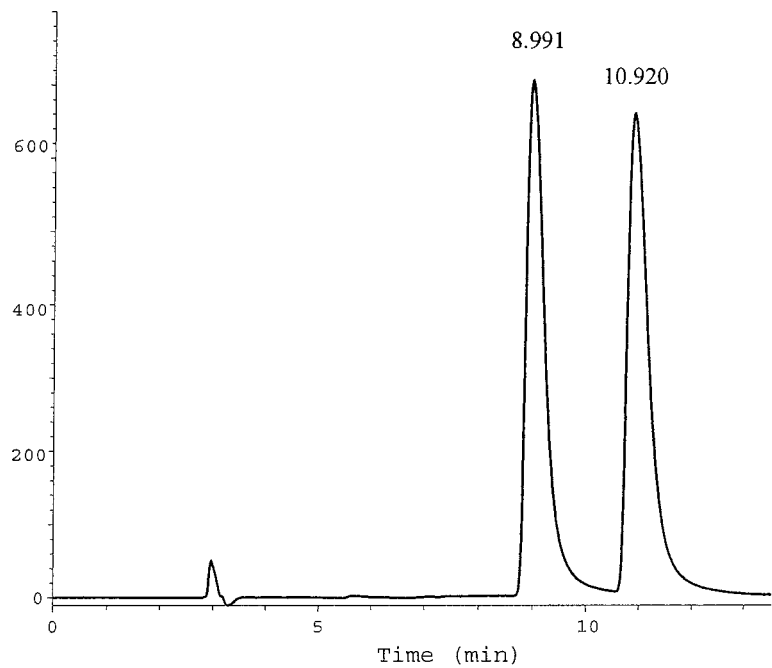
FIG. 4. Chromatogram obtained for TR-2 (benzoine) on a column filled with CSP-4
Figure 5:
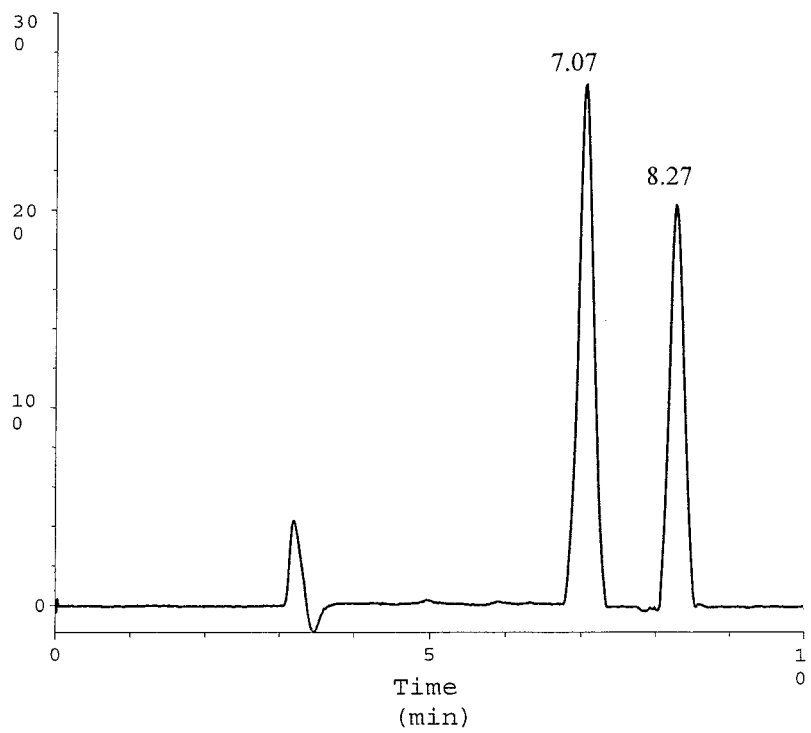
FIG. 5. Chromatogram obtained for TR-4 (Tröger's base) on a column filled with CSP-2
Figure 6:
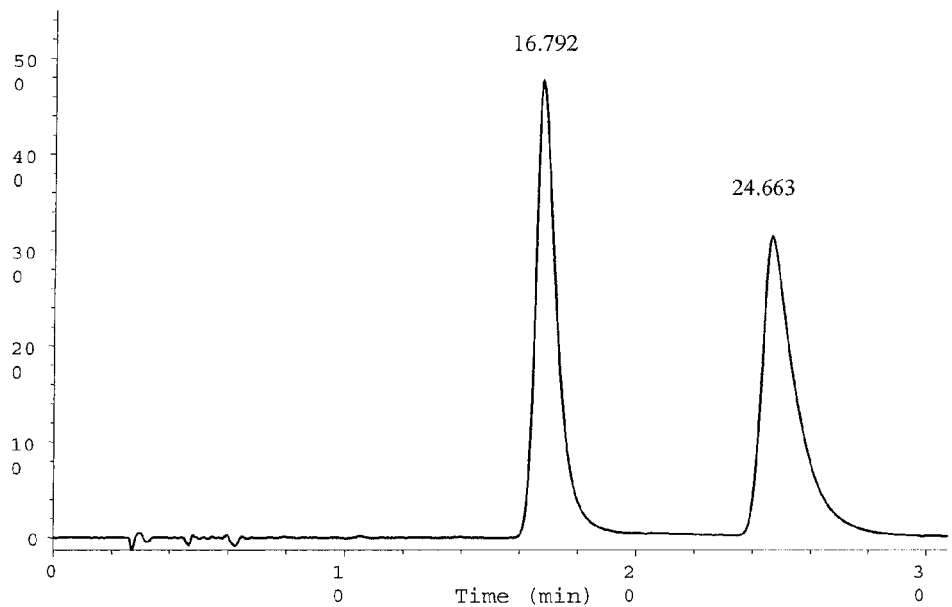
FIG. 6. Chromatogram obtained for TR-7 on a column filled with CSP-2
Figure 7:
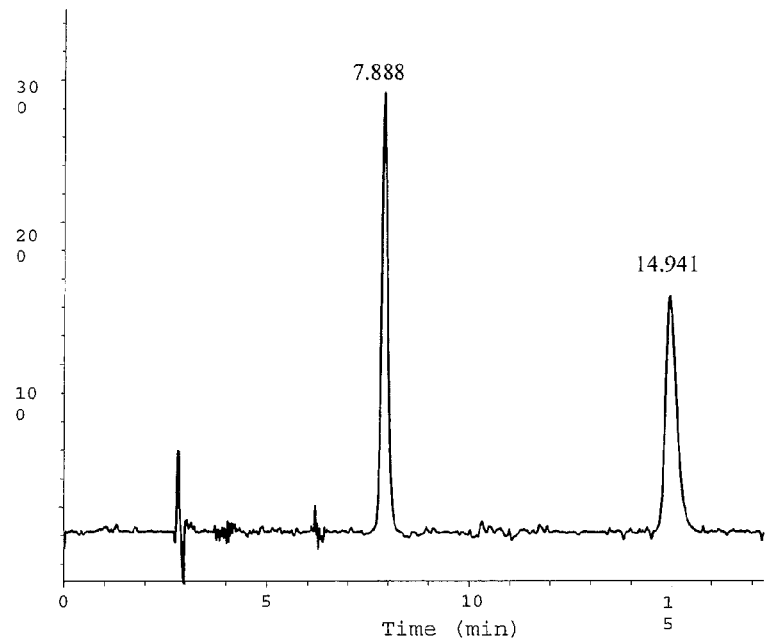
FIG. 7. Chromatogram obtained for TR-9 on a column filled with CSP-4

Enantiomers of test racemates 1-18, FIG. 3, were separated on analytical HPLC columns (250 mm×4.6 mm) loaded with CSP-1 and CSP-2. Results typically show good performance, i.e., higher enantioseparation of the column loaded with CSP-2 over CSP-1, and the selected results obtained on CSP-2 are shown in Tables 1 and 2.

TABLE 1

Enantiomer separations for some test racemate on a column filled with CSP-2 (250 mm × 4.6 mm ID), with hexane:i-PrOH = 9:1 as the mobile phase and a flow of 1 ml/min, 254 nm.

| TR | $t_{R1}$/min | $t_{R2}$/min | $k_1$ | $\alpha$ | $R_S$ |
|---|---|---|---|---|---|
| TR-1 | 5.98 | 6.93 | 0.97 | 1.32 | 2.16 |
| TR-2 | 15.20 | 17.20 | 4.00 | 1.17 | 1.76 |
| TR-3 | 11.41 | 11.62 | 2.76 | 1.03 | 0.32 |
| TR-4 | 7.07 | 8.27 | 1.33 | 1.30 | 2.45 |
| TR-5 | 9.93 | 11.63 | 2.27 | 1.25 | 2.18 |
| TR-6 | 9.71 | 12.91 | 2.19 | 1.48 | 3.20 |
| TR-8 | 27.80 | 30.54 | 8.17 | 1.11 | 1.61 |

TABLE 2

Enantiomer separations for some test racemate on the column filled with CSP-2 (250 mm × 4.6 mm ID), with hexane:i-PrOH = 7:3 as the mobile phase and a flow of 1 ml/min, 254 nm.

| TR | $t_{R1}$/min | $t_{R2}$/min | $k_1$ | $\alpha$ | $R_S$ |
|---|---|---|---|---|---|
| TR-7 | 16.79 | 24.66 | 4.47 | 1.57 | 4.20 |
| TR-9 | 8.19 | 10.90 | 1.83 | 1.52 | 4.40 |
| TR-12 | 7.13 | 9.48 | 1.46 | 1.56 | 3.76 |
| TR-13 | 28.90 | 37.21 | 8.99 | 1.32 | 3.28 |
| TR-14 | 16.62 | 17.63 | 4.74 | 1.07 | 0.65 |
| TR-15 | 17.02 | 17.81 | 4.88 | 1.06 | 0.45 |
| TR-17 | 24.30 | 27.62 | 7.41 | 1.15 | 1.95 |

EXAMPLE 20

Enantiomer Separation on CSP-3 and CSP-4

Enantiomers of test racemates 1-18, FIG. 3, were separated on analytical HPLC columns (250 mm×4.6 mm) filled with CSP-3 and CSP-4. Results show typically good performance, i.e., higher enantioseparation of the column loaded with CSP-4 over CSP-3 and the selected results obtained on CSP-4 are shown in Tables 3 and 4. Generally CSP-4, compared to other stationary phases mentioned herewith, separates more enantiomers, but in some individual cases CSP-2 is more efficient. Selected chromatograms are shown in FIGS. 4-7.

TABLE 3

Enantiomer separations for some test racemate on the column filled with CSP-4 (250 mm × 4.6 mm ID), with hexane:i-PrOH = 9:1 as the mobile phase and a flow of 1 ml/min, 254 nm.

| TR | $t_{R1}$/min | $t_{R2}$/min | $k_1$ | $\alpha$ | $R_S$ |
|---|---|---|---|---|---|
| TR-1 | 4.61 | 5.31 | 0.56 | 1.42 | 2.84 |
| TR-2 | 8.99 | 10.92 | 2.04 | 1.32 | 2.69 |
| TR-4 | 5.71 | 6.74 | 0.93 | 1.37 | 2.45 |
| TR-5 | 7.01 | 7.51 | 1.37 | 1.12 | 0.81 |
| TR-6 | 8.16 | 8.84 | 1.76 | 1.13 | 1.31 |
| TR-8 | 14.02 | 15.63 | 3.75 | 1.14 | 2.86 |

TABLE 4

Enantiomer separations for some test racemate on the column filled with CSP-4 (250 mm × 4.6 mm ID), with hexane:i-PrOH = 7:3 as the mobile phase and a flow of 1 ml/min, 254 nm.

| TR | $t_{R1}$/min | $t_{R2}$/min | $k_1$ | $\alpha$ | $R_S$ |
|---|---|---|---|---|---|
| TR-9 | 6.16 | 10.29 | 1.18 | 2.24 | 11.01 |
| TR-10 | 9.48 | 14.36 | 2.36 | 1.73 | 8.34 |
| TR-11 | 27.16 | 39.90 | 8.63 | 1.52 | 4.91 |
| TR-12 | 5.96 | 7.84 | 1.11 | 1.60 | 5.45 |
| TR-13 | 21.27 | 28.10 | 6.54 | 1.38 | 4.69 |
| TR-14 | 11.78 | 13.88 | 3.18 | 1.23 | 3.13 |
| TR-15 | 11.61 | 14.50 | 3.12 | 1.33 | 3.40 |
| TR-16 | 9.62 | 13.41 | 2.41 | 1.56 | 6.48 |
| TR-17 | 19.20 | 19.81 | 5.81 | 1.04 | 0.35 |
| TR-18 | 13.68 | 17.03 | 3.68 | 1.31 | 2.76 |

EXAMPLE 21

Enantiomer Separation of the Non-Steroidal Anti-Inflammatory Drugs TR 19-23

Figure 8:
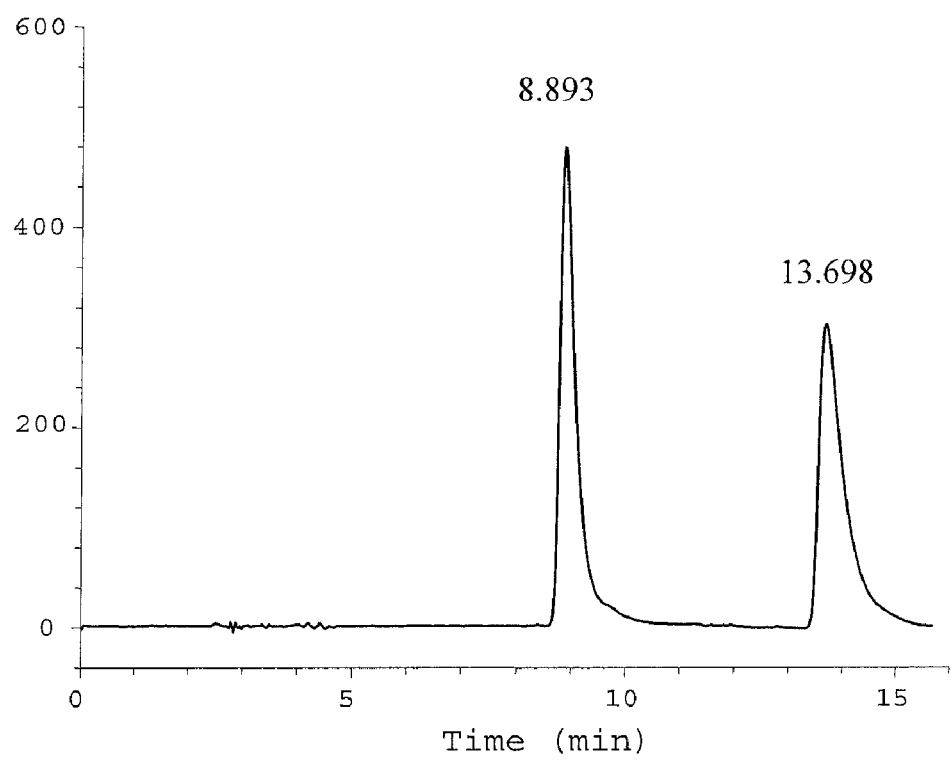
FIG. 8. Chromatogram obtained for TR-19 (naproxen) on a column filled with CSP-4

Enantiomers of test racemates TR 19-23, of known drugs from the non-steroidal anti-inflammatory group, were separated on analytical HPLC columns (250 mm×4.6 mm), filled with CSP-4 or CSP-3. Since these compounds are structurally free carboxyl acids, it was necessary to use a polar mobile phase containing a certain amount of ammonium acetate. Results obtained by the enantioselective separation of these compounds are shown in Table 5 and the chromatogram achieved for the enantiomers of naproxen is shown in FIG. 8.

TABLE 5

Enantiomer separations for test racemate TR 20-23 on the column filled with CSP-3 (250 mm × 4.6 mm ID), with hexane:2-PrOH = 8:2 + 1 g/L NH$_4$OAc as the mobile phase, 1 ml/min, 254 nm.

| TR | $t_{R1}$/min | $t_{R2}$/min | $k_1$ | $\alpha$ | $R_S$ |
|---|---|---|---|---|---|
| TR-20 (ketoprofen) | 39.02 | 46.71 | 12.2 | 1.21 | 1.33 |
| TR-21 (fenoprofen) | 10.01 | 14.03 | 2.42 | 1.55 | 3.51 |
| TR-22 (flurbiprofen) | 15.02 | 20.16 | 4.10 | 1.42 | 2.44 |
| TR-23 (ibuprofen) | 9.14 | 11.22 | 2.10 | 1.33 | 2.58 |

What is claimed is:

1. Chiral stationary phases, having the structure CSP I:

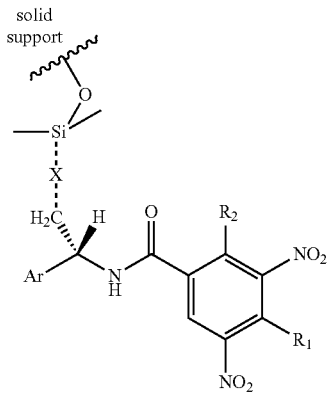

CSP I where $R_1$ and $R_2$ indicate hydrogen atom or methyl group, Ar indicates a group selected among phenyl, 3,5-dimetylphenyl, 1-naphthyl or 9-antryl, and X indicates (—$CH_2$—)$_n$, where n=0, 1, or 2, as a linker which is covalently bound to a solid support for chromatography, and (S)-absolute configuration of selector is randomly selected, and may also be (R)-configuration.

2. Chiral stationary phases according to claim 1, where n=1.

3. Chiral stationary phases according to claim 2, wherein the solid support is an inorganic material.

4. Chiral stationary phases according to claim 3, wherein the solid support is a silica gel, aluminum oxide, kaoline, titanium oxide, magnesium oxide, silicate or a synthetic polymer.

5. Chiral stationary phases, having the structure CSP I:

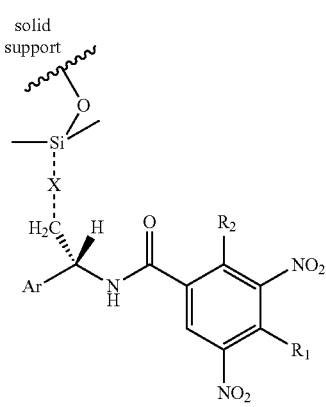

CSP I where $R_1$ and $R_2$ indicate hydrogen atom or methyl group, Ar indicates a group selected among phenyl, 3,5-dimetylphenyl, 1-naphthyl or 9-antryl, and X indicates (—$CH_2$—)$_n$, where n=1, as a linker which is covalently bound to a solid support for chromatography, and (S)-absolute configuration of selector is randomly selected, and may also be (R)-configuration.

6. Chiral stationary phases according to claim 5, wherein the solid support is an inorganic material.

7. Chiral stationary phases according to claim 6, wherein the solid support is a silica gel, aluminum oxide, kaoline, titanium oxide, magnesium oxide, silicate or a synthetic polymer.

* * * * *